US010201188B2

(12) United States Patent
Lin

(10) Patent No.: US 10,201,188 B2
(45) Date of Patent: Feb. 12, 2019

(54) ELECTRONIC CIGARETTE AND METHOD OF ASSEMBLING ELECTRONIC CIGARETTE

(71) Applicant: Guangrong Lin, Guangdong (CN)

(72) Inventor: Guangrong Lin, Guangdong (CN)

( * ) Notice: Subject to any disclaimer, the term of this patent is extended or adjusted under 35 U.S.C. 154(b) by 69 days.

(21) Appl. No.: 15/303,745

(22) PCT Filed: Mar. 20, 2015

(86) PCT No.: PCT/CN2015/074710
§ 371 (c)(1),
(2) Date: Oct. 13, 2016

(87) PCT Pub. No.: WO2015/158195
PCT Pub. Date: Oct. 22, 2015

(65) Prior Publication Data
US 2017/0035117 A1 Feb. 9, 2017

(30) Foreign Application Priority Data

Apr. 16, 2014 (CN) ..................... 2014 2 0184089 U

(51) Int. Cl.
*F16B 7/20* (2006.01)
*H01M 2/10* (2006.01)
*A24F 47/00* (2006.01)
*A61M 15/06* (2006.01)
(52) U.S. Cl.
CPC ............ *A24F 47/008* (2013.01); *A24F 47/00* (2013.01); *A61M 15/06* (2013.01); *F16B 7/20* (2013.01); *H01M 2/1055* (2013.01); *H01M 2220/30* (2013.01)

(58) Field of Classification Search
None
See application file for complete search history.

(56) References Cited

U.S. PATENT DOCUMENTS 4,911,573 A * 3/1990 Pietro ................. B25G 3/16
285/361
2013/0180410 A1* 7/2013 Jing ................. A47J 31/407
99/295

(Continued)

FOREIGN PATENT DOCUMENTS

CN 102389166 A 3/2012
CN 203523808 U 4/2014

OTHER PUBLICATIONS

International Search Report of PCT Patent Application No. PCT/CN2015/074710 dated Jun. 17, 2015.

*Primary Examiner* — Ibrahime A Abraham
*Assistant Examiner* — Gyounghyun Bae

(57) ABSTRACT

Disclosed is an electronic cigarette including a battery connector and a vaporizer connector, wherein the battery connector comprises two recessed L-shaped grooves, and the vaporizer connector comprises two symmetrically-arranged protrusions. After the battery connector has been twist-lock connected with the vaporizer connector, the L-shaped grooves of the battery connector tightly engage with the protrusions of the vaporizer connector, positive and negative electrodes of a battery assembly are electrically connected to two electrodes of a vaporizer electrode assembly.

8 Claims, 10 Drawing Sheets

(56) References Cited

U.S. PATENT DOCUMENTS

| | | | |
|---|---|---|---|
| 2014/0041658 A1* | 2/2014 | Goodman | F22B 1/282 128/203.14 |
| 2014/0174458 A1* | 6/2014 | Katz | A24F 47/008 131/200 |
| 2014/0261493 A1* | 9/2014 | Smith | A24F 47/008 131/328 |
| 2015/0013701 A1* | 1/2015 | Liu | A24F 47/008 131/329 |
| 2015/0027467 A1* | 1/2015 | Liu | A24F 47/008 131/329 |
| 2015/0059784 A1* | 3/2015 | Liu | A24F 47/008 131/329 |
| 2015/0201674 A1* | 7/2015 | Dooly | A24F 47/008 53/432 |
| 2015/0223522 A1* | 8/2015 | Ampolini | A24F 47/008 131/328 |
| 2016/0338405 A1* | 11/2016 | Liu | A24F 47/008 |
| 2017/0071252 A1* | 3/2017 | Liu | A24F 47/008 |
| 2017/0172207 A1* | 6/2017 | Liu | A24F 47/008 |

* cited by examiner

ELECTRONIC CIGARETTE AND METHOD OF ASSEMBLING ELECTRONIC CIGARETTE

FIELD OF THE INVENTION

The present invention relates to an electronic cigarette and a method of assembling an electronic cigarette.

BACKGROUND OF THE INVENTION

A vaporizer assembly and a battery assembly of an existing electronic cigarette having a non-circular cross section are usually connected via a nested structure, other connecting structures are neither user-friendly nor convenient for the assembly and disassembly of the components of an electronic cigarette having a non-circular cross section.

SUMMARY OF THE INVENTION

The present invention aims to provide an electronic cigarette comprising a vaporizer assembly and a battery assembly connected via a twist lock joint. Such twist lock joint is very convenient for the assembly and disassembly of components of an electronic cigarette having a non-circular cross section. Another object of the present invention is to provide a convenient method of assembling an electronic cigarette.

A technical solution of the present invention is an electronic cigarette comprising a battery assembly and a vaporizer assembly abutting the battery assembly, wherein a battery connector at a connecting end of the battery assembly and a vaporizer connector at a connecting end of the vaporizer assembly are connected via a twist lock joint, an electrode of the battery connector is electrically connected to an electrode of the vaporizer connector; the battery connector is consisted of a tube body and a protruding platform formed on one end of the tube body and having a cross-sectional area smaller than the tube body, wherein a circular cavity is provided at the center of the protruding platform, two recessed L-shaped grooves are radially and symmetrically formed in an inner wall of the circular cavity, a through hole is opened at a bottom of the circular cavity, positive and negative electrodes of the battery assembly are protruded out from the through hole, an outer wall of the protruding platform has a protrusion for snap fitting with a corresponding protrusion formed at an inner wall of one end of an outer tube of the vaporizer assembly; the vaporizer connector comprises a tube body and a circular protruding platform formed on one end of the tube body and having a cross-sectional area smaller than the tube body, two symmetrically-arranged protrusions protrude radially outward from an outer wall of the circular protruding platform, a center of the circular protruding platform is provided with a vaporizer electrode assembly comprising two electrodes, after the battery connector has been twist-lock connected with the vaporizer connector, the circular cavity of the battery connector exactly receives the circular protruding platform of the vaporizer connector, the L-shaped grooves of the battery connector tightly engage with the protrusions of the vaporizer connector, the positive and negative electrodes of the battery assembly are electrically connected to the two electrodes of the vaporizer electrode assembly.

Preferably, the L-shaped groove is consisted of a vertical groove and an arc-shaped groove starting from a bottom half of the vertical groove and extending along a portion of the circumference of the inner wall of the circular cavity, wherein a height of the arc-shaped groove is slightly and gradually decreased.

Preferably, a lug is protruded downward from a top edge of the arc-shaped groove for locking purpose.

Preferably, the protrusion of the vaporizer connector has a concave portion configured to engage with the lug at the top edge of the arc-shaped groove.

Preferably, the positive and negative electrodes of the battery assembly are rod-like and retractable electrodes.

Preferably, the vaporizer electrode assembly is consisted of a column-shaped electrode fixer inserted into a central through hole of the circular protruding platform, a rod-like electrode having a protruding ring at one end thereof and inserted into a central through hole of the column-shaped electrode fixer, and a semi-annular electrode inserted into an annular cavity recessed along an outer circumference of the central through hole of the electrode fixer.

Preferably, that the vaporizer electrode assembly is consisted of a column-shaped electrode fixer inserted into a central through hole of the circular protruding platform, a rod-like electrode having a protruding ring at one end thereof and inserted into a central through hole of the column-shaped electrode fixer, and a full-annular electrode inserted into an annular cavity recessed along an outer circumference of the central through hole of the electrode fixer.

Preferably, the battery assembly, the vaporizer assembly and the outer tube of the vaporizer assembly all have non-circular cross sections.

Preferably, the non-circular cross section is oval cross section.

Preferably, an angle between the major axis X of an oval end surface of the oval protruding platform of the battery connector and a straight line between two midpoints of two vertical grooves of the symmetrically-arranged L-shaped grooves is an acute angle.

Another technical solution of the present invention is a method of assembling an electronic cigarette comprising a battery assembly and a vaporizer assembly abutting the battery assembly, wherein the method comprises aligning a protrusion of a vaporizer connector to an L-shaped groove of a battery connector; inserting a circular protruding platform of the vaporizer assembly into a circular cavity of the battery connector; twisting the vaporizer connector to a locking position so as to enable positive and negative electrodes of the battery connector to be electrically connected to a semi-annular electrode and a rod-like electrode of the vaporizer connector, wherein the rod-like electrode has a protruding ring at one end thereof; sheathing the vaporizer assembly with an outer tube of the vaporizer assembly; and engaging a protrusion of an outer wall of a protruding platform with a corresponding protrusion of the outer tube of the vaporizer assembly to complete a snap fit therebetween.

The technical solutions of the present invention have the following advantage. The twist lock joint between the vaporizer assembly and the battery assembly can be employed for various types of electronic cigarettes having non-circular cross section.

Figure 1:
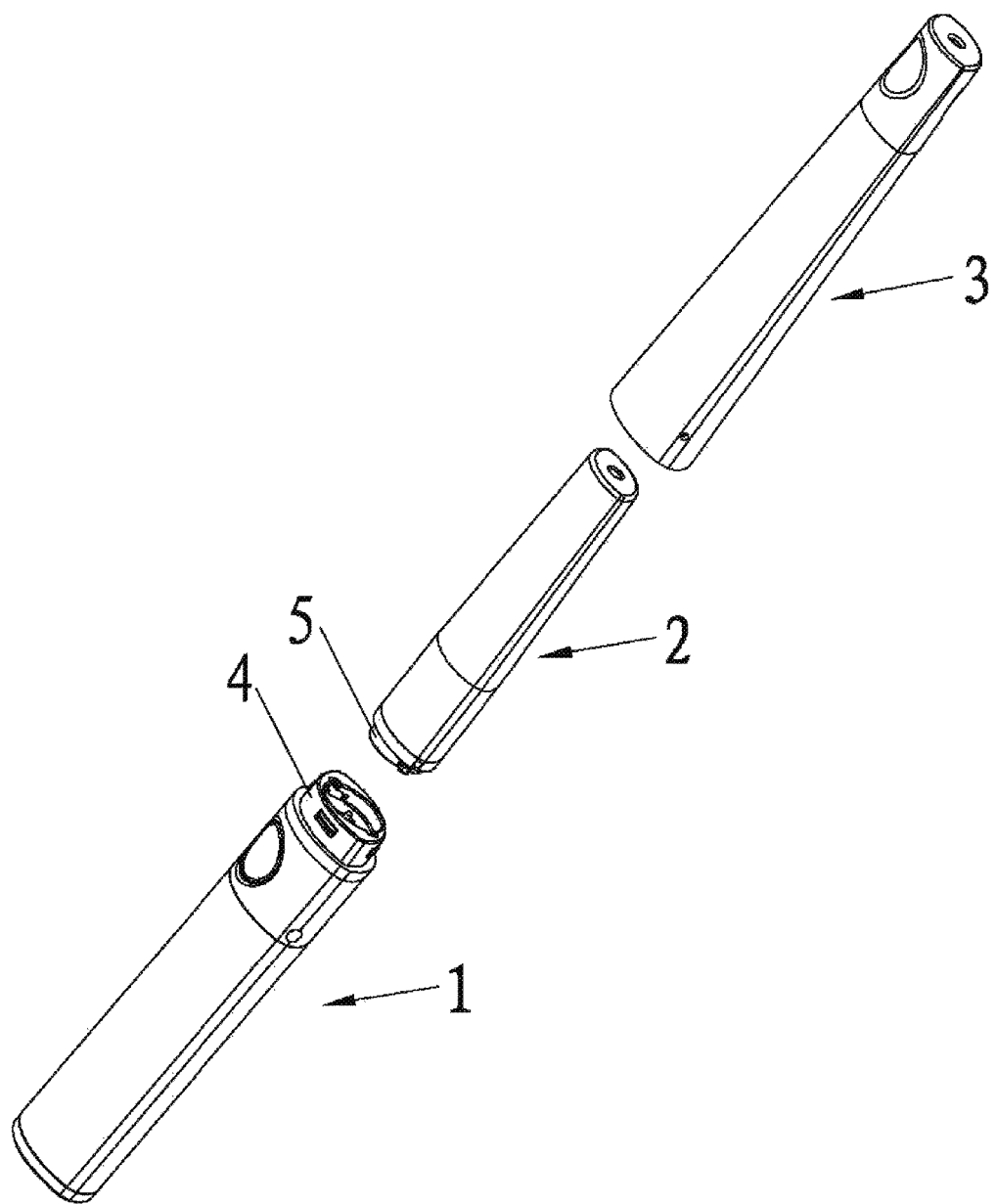
FIG. 1 is a perspective exploded view of an electronic cigarette of the present invention.

LIST OF REFERENCE NUMERALS OF MAIN COMPONENTS 1 battery assembly
2 vaporizer assembly
3 outer tube of vaporizer assembly
4 battery connector
41 electrode
42 tube body
421 protruding platform
422 circular cavity
4221 through hole
4222 protrusion
423 L-shaped groove
4231 vertical groove
4232 arc-shaped groove
4233 lug
5 vaporizer connector
51 tube body
511 air inlet
52 protrusion
521 concave portion
53 circular protruding platform
54 central through hole
6 vaporizer electrode assembly
61 semi-annular electrode
611 electrode plate
612 insertion electrode plate
62 rod-like electrode
63 electrode fixer
631 annular cavity
632 central through hole
633 insertion groove

DETAILED DESCRIPTION OF ILLUSTRATED EMBODIMENTS

Various preferred embodiments will now be described with reference to the figures.

Figure 2:
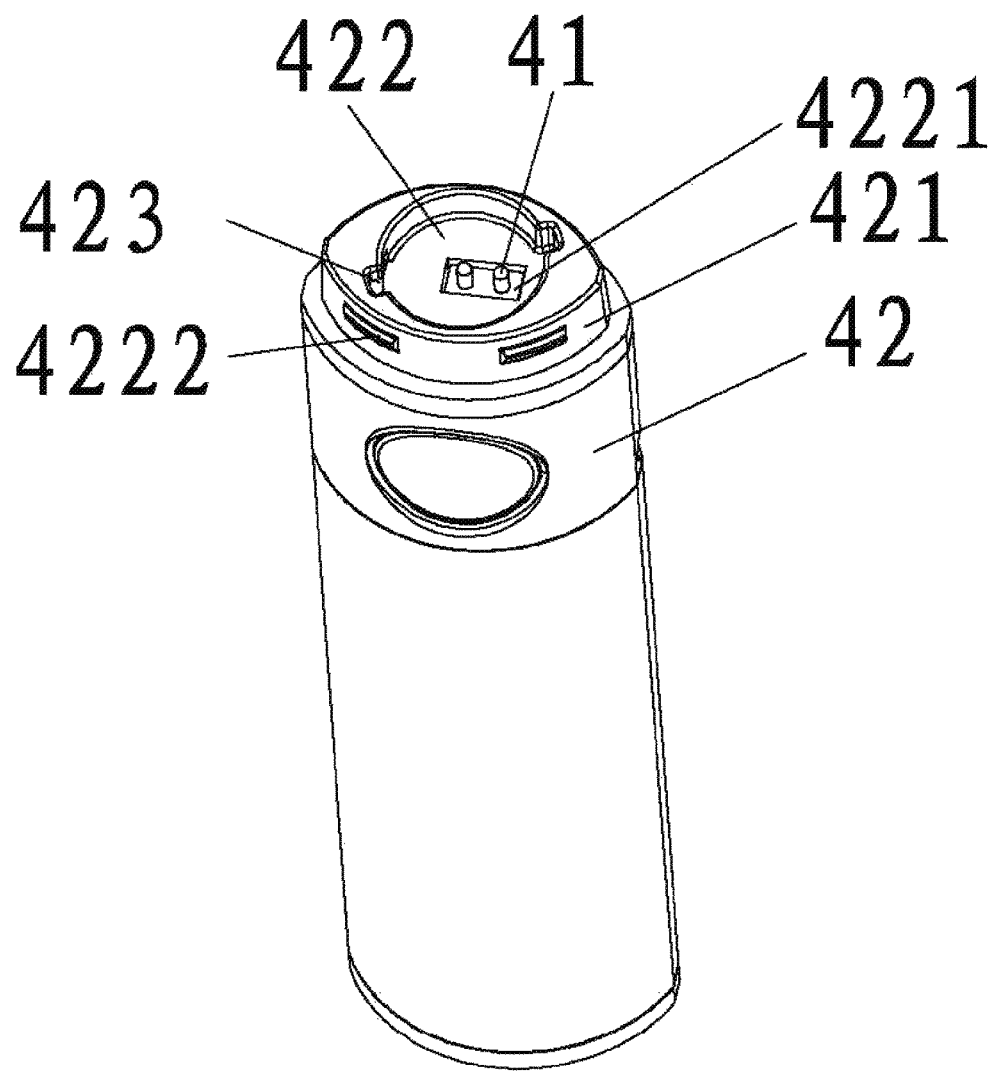
FIG. 2 is a schematic view showing a battery connector of an electronic cigarette of the present invention.
Figure 6:
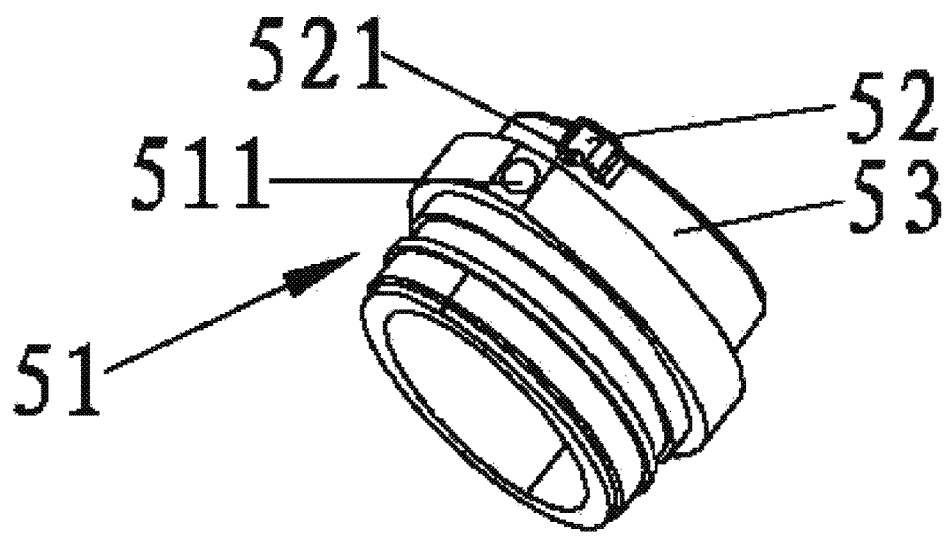
FIG. 6 is a schematic view showing a vaporizer connector of an electronic cigarette of the present invention.

Referring to FIGS. 1, 2 and 6, an electronic cigarette comprises a battery assembly 1, a vaporizer assembly 2 abutting the battery assembly 1, and an outer tube 3 of the vaporizer assembly 2, the outer tube 3 sheathing the vaporizer assembly 2 and having a snap fit with the battery assembly 1. A battery connector 4 at a connecting end of the battery assembly 1 and a vaporizer connector 5 at a connecting end of the vaporizer assembly 2 are connected via a twist lock joint. An electrode 41 of the battery connector 4 is electrically connected to a semi-annular electrode 61 and a rod-like electrode 62 of the vaporizer connector 5, wherein the rod-like electrode 62 has a protruding ring at one end thereof.

Referring to FIG. 1, the battery assembly 1, the vaporizer assembly 2 and the outer tube 3 of the vaporizer assembly 2 all have oval cross sections.

Figure 3:
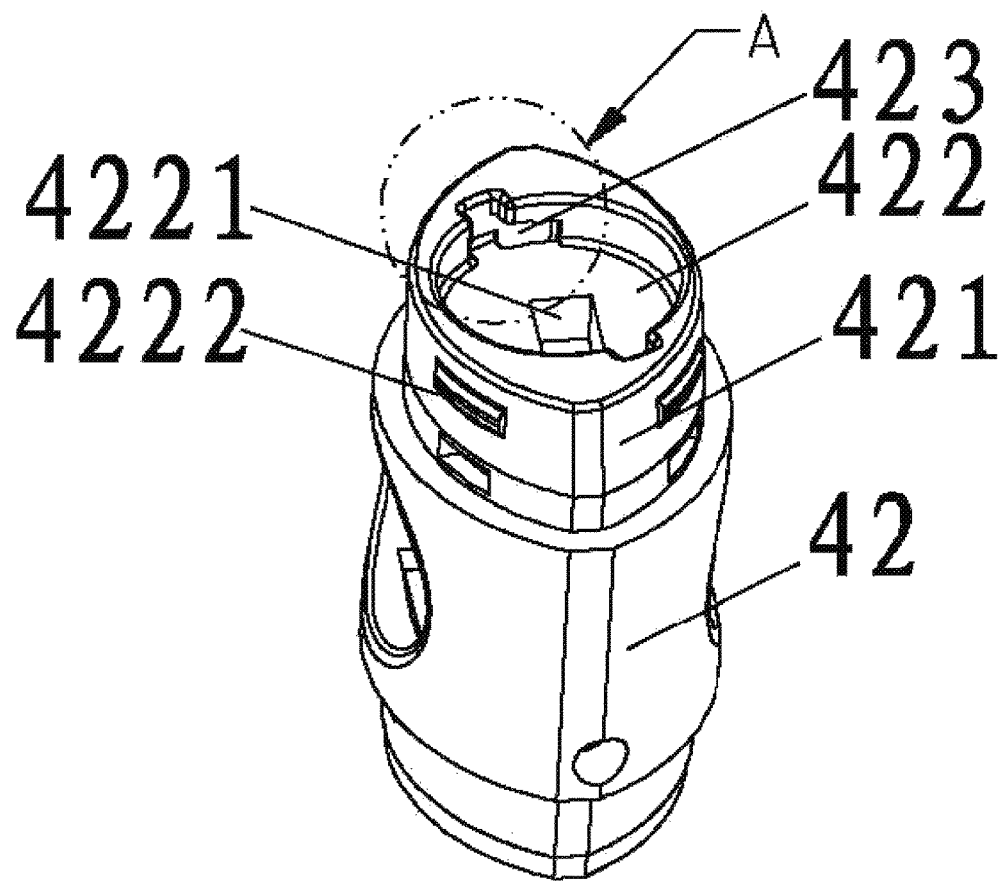
FIG. 3 is another schematic view showing a battery connector of an electronic cigarette of the present invention.

Referring to FIGS. 2 and 3, the battery connector 4 is consisted of a tube body 42, and a protruding platform 421 formed on one end of the tube body 42 and having a cross-sectional area smaller than the tube body 42. A circular cavity 422 is provided at the center of the protruding platform 421. Two recessed L-shaped grooves 423 are radially and symmetrically formed in an inner wall of the circular cavity 422. A through hole 4221 is opened at a bottom of the circular cavity 422. Positive and negative electrodes 41 of the battery assembly 1 are protruded out from the through hole 4221. An outer wall of the protruding platform 421 has a protrusion 4222 for snap fitting with a corresponding protrusion (not shown in the figures) formed at an inner wall of one end of the outer tube 3 of the vaporizer assembly 2.

Figure 4:
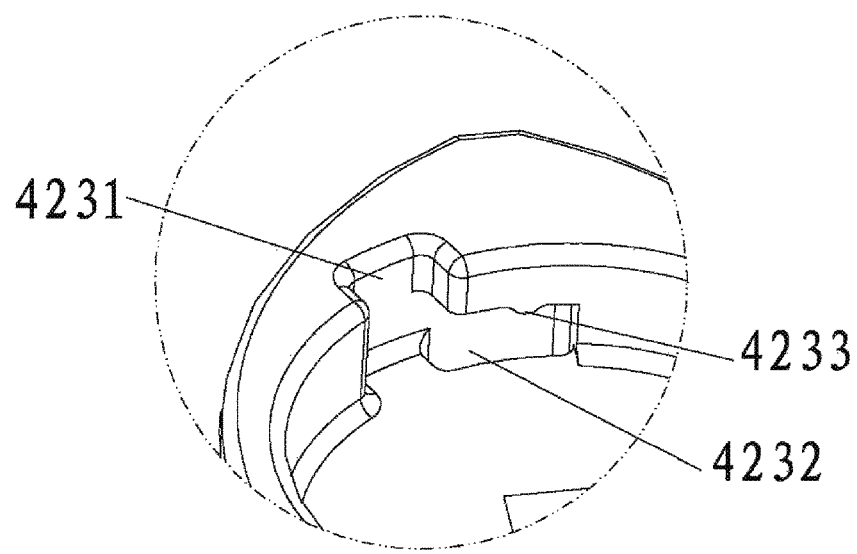
FIG. 4 is an enlarged partial view of the battery connector shown in FIG. 3.

Referring to FIG. 4, the L-shaped groove 423 is consisted of a vertical groove 4231 and an arc-shaped groove 4232 smoothly communicating with the vertical groove 4231. The arc-shaped groove 4232 starts from a bottom half of the vertical groove 4231 and extends along a portion of the circumference of the inner wall of the circular cavity 422. A lug 4233 is protruded downward from a top edge of the arc-shaped groove 4232 for locking purpose.

Figure 5:
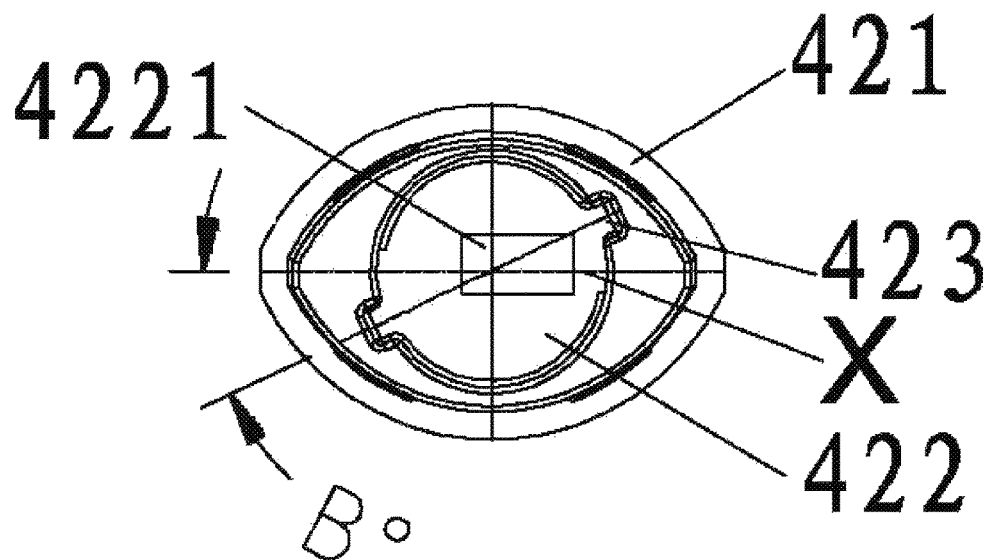
FIG. 5 is a schematic view showing an acute angle between the major axis X of an oval end surface of a protruding platform of a battery connector and a straight line between two midpoints of two vertical grooves of two symmetrically-arranged L-shaped grooves.

Referring to FIG. 5, an angle between the major axis X of an oval end surface of the oval protruding platform 421 of the battery connector 4 and a straight line between two midpoints of the two vertical grooves 4231 of the symmetrically-arranged L-shaped grooves 423 is an acute angle.

Figure 7:
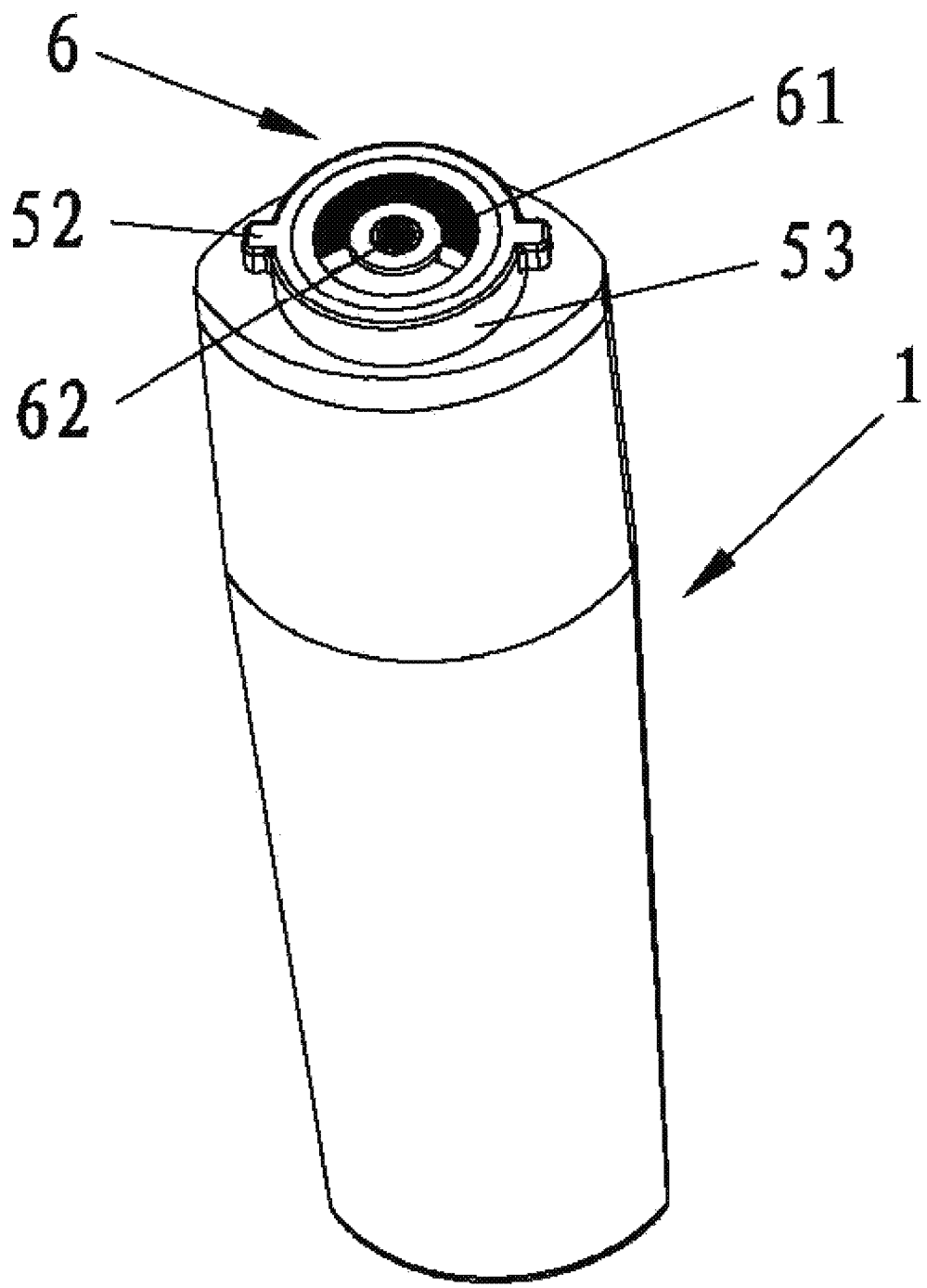
FIG. 7 is another schematic view showing a vaporizer connector of an electronic cigarette of the present invention.

Referring to FIGS. 6 and 7, the vaporizer connector 5 comprises a tube body 51, an air inlet 511 of an air passage opened in the tube body 51, and a circular protruding platform 53 formed on one end of the tube body 51 and having a cross-sectional area smaller than the tube body 51. Two symmetrically-arranged protrusions 52 protrude radially outward from an outer wall of the circular protruding platform 53. A center of the circular protruding platform 53 is provided with a vaporizer electrode assembly 6. The vaporizer electrode assembly 6 comprises two electrodes 61, 62.

Figure 8:
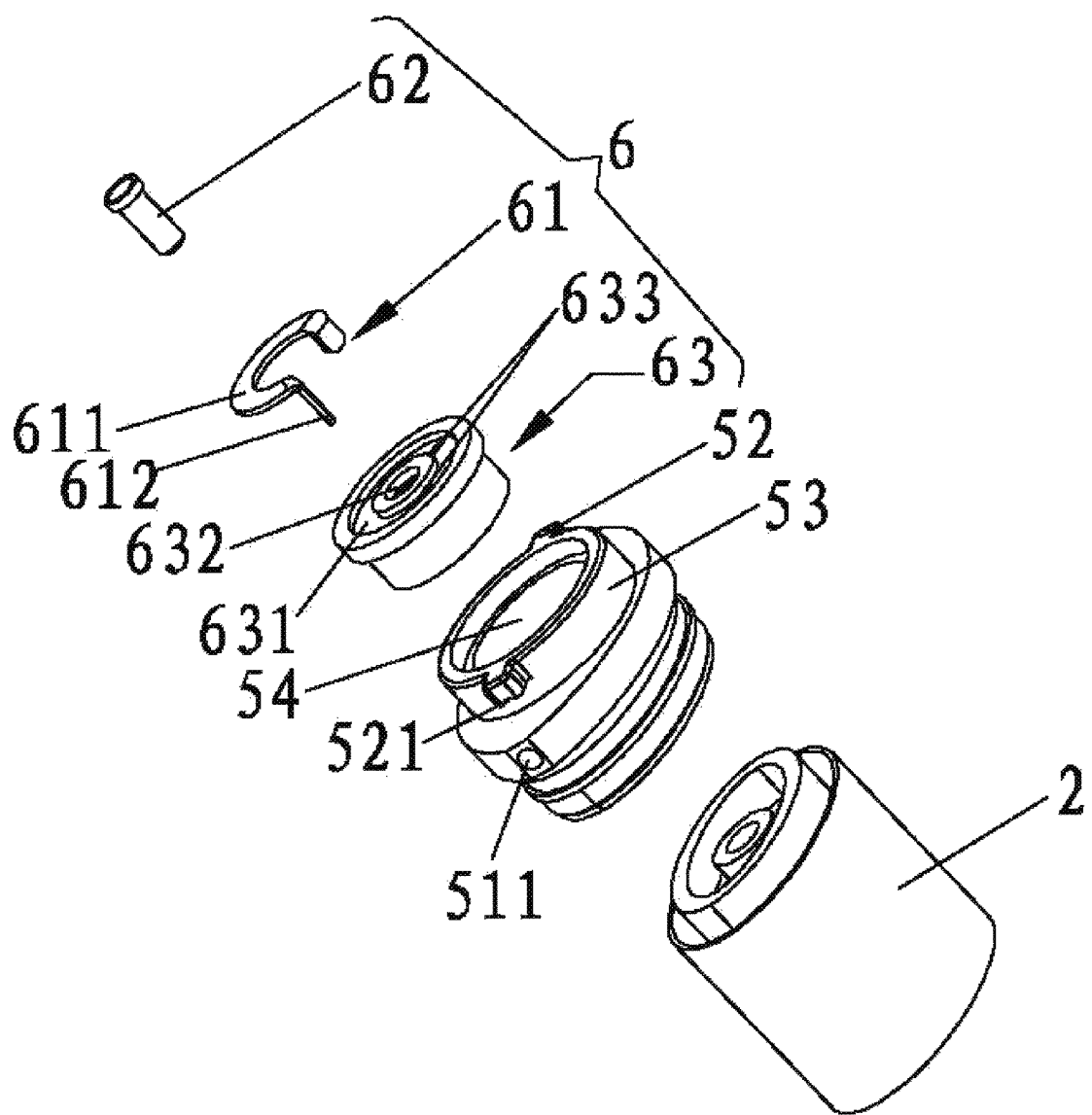
FIG. 8 is a perspective exploded view of a vaporizer electrode assembly of an electronic cigarette of the present invention.
Figure 9:
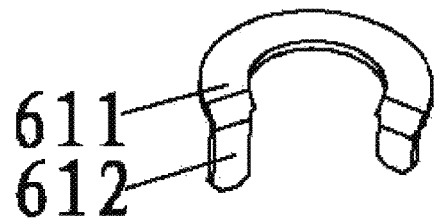
FIG. 9 is an enlarged schematic view showing a semi-annular electrode of the vaporizer electrode assembly shown in FIG. 8.

Referring to FIGS. 8 and 9, the vaporizer electrode assembly 6 is consisted of a column-shaped electrode fixer 63 inserted into a central through hole 54 of the circular protruding platform 53, a rod-like electrode 62 having a protruding ring at one end thereof and inserted into a central through hole 632 of the column-shaped electrode fixer 63, and a semi-annular electrode 61 inserted into both an annular cavity 631 recessed along an outer circumference of the central through hole 632 of the electrode fixer 63 and an insertion groove 633 provided at a bottom of the annular cavity 631. The semi-annular electrode 61 is consisted of a semi-annular electrode plate 611 and two insertion electrode plates 612 protruding perpendicularly from two ends of the semi-annular electrode plate 611.

Figure 10:
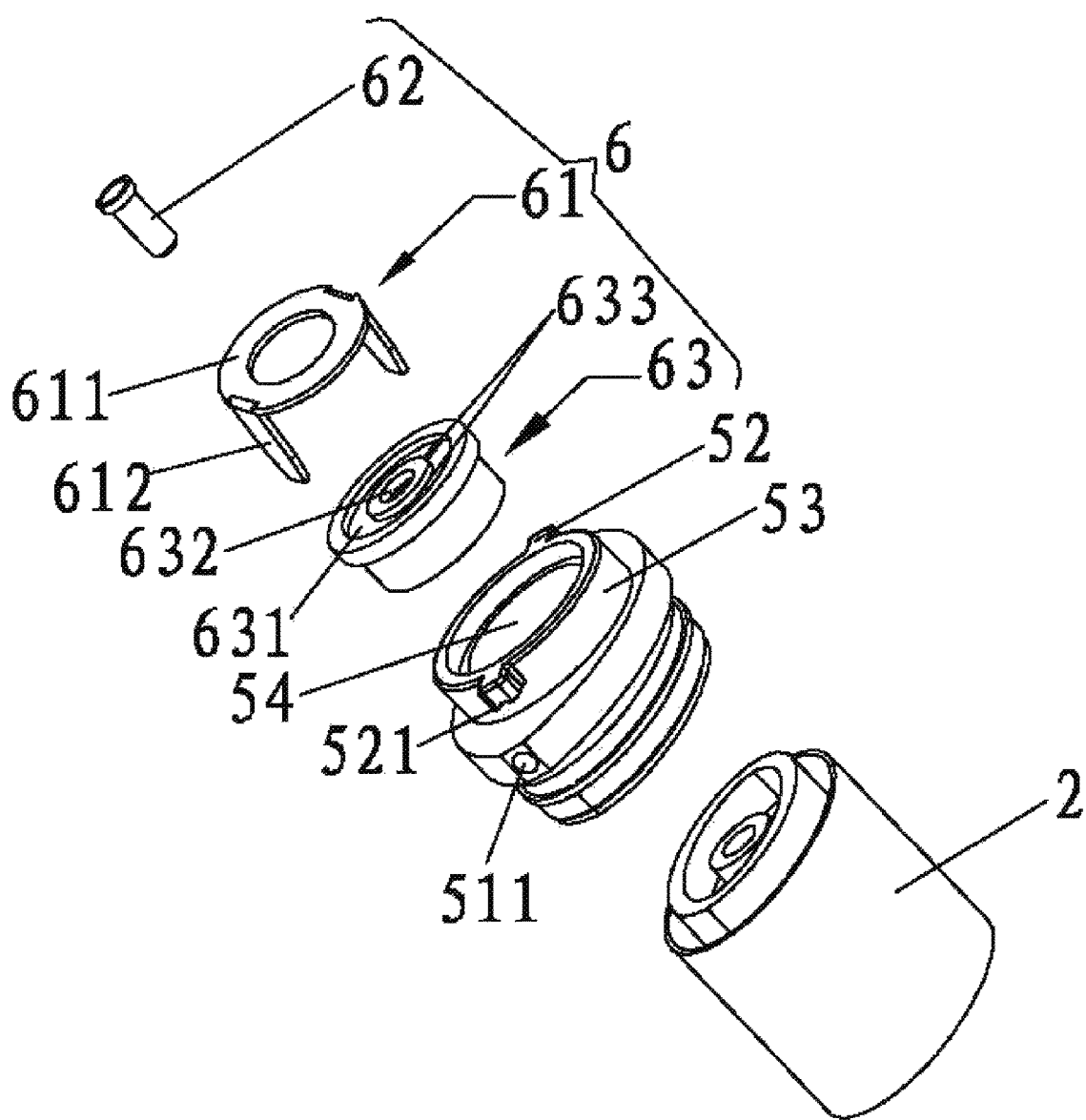
FIG. 10 is another perspective exploded view of a vaporizer electrode assembly of an electronic cigarette of the present invention.
Figure 11:
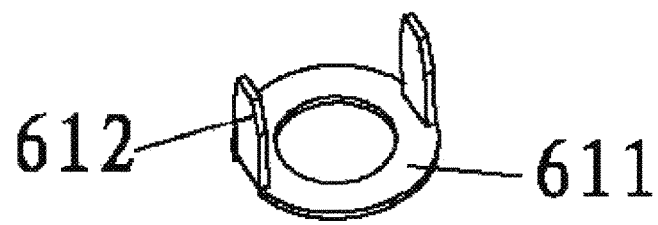
FIG. 11 is a full-annular electrode of the vaporizer electrode assembly shown in FIG. 10
Figure 12:
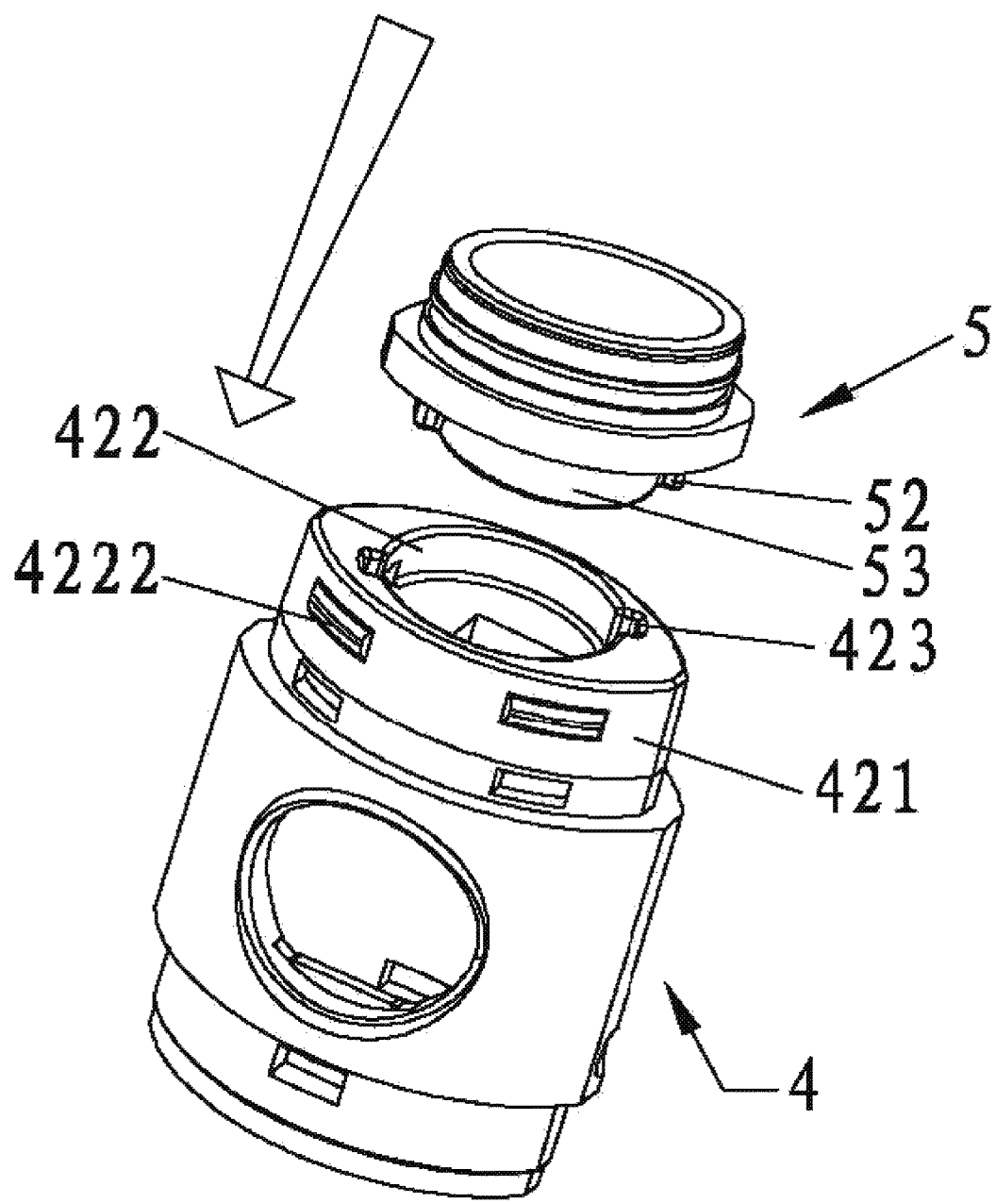
FIGS. 12, 13 and 14 are schematic views showing a twist-lock mechanism between a vaporizer assembly and a battery assembly of an electronic cigarette of the present invention.
Figure 13:
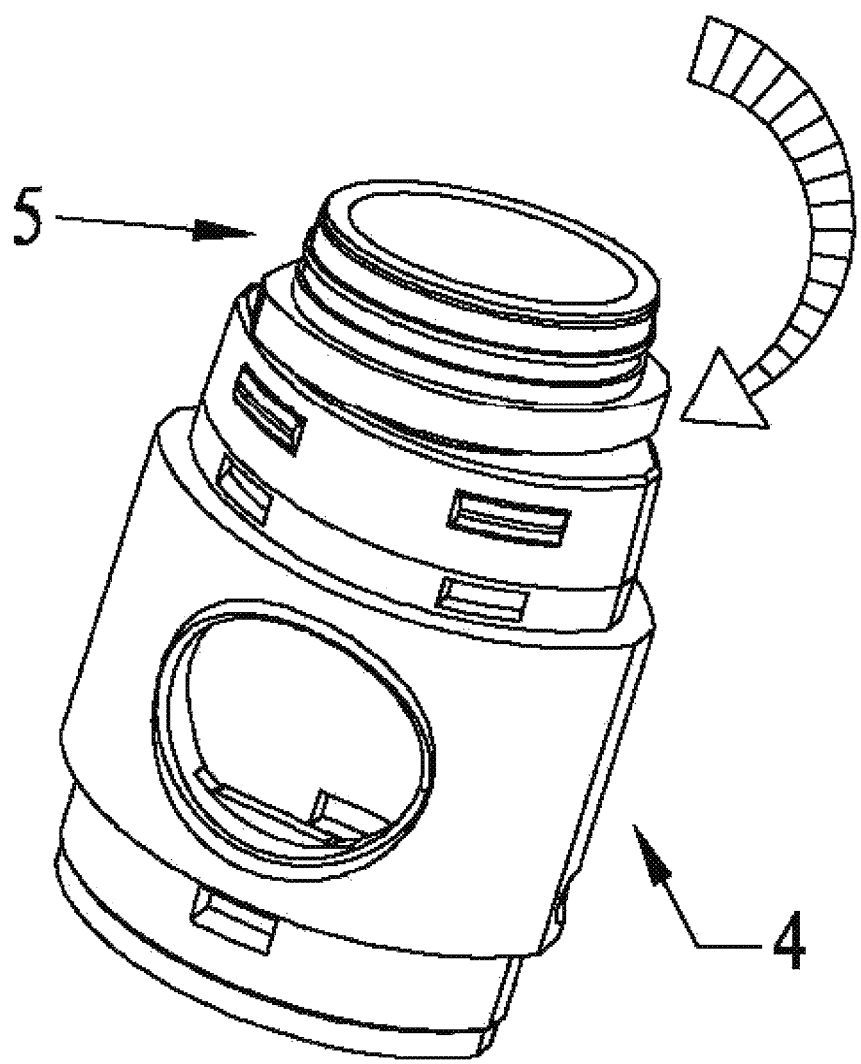
Figure 14:
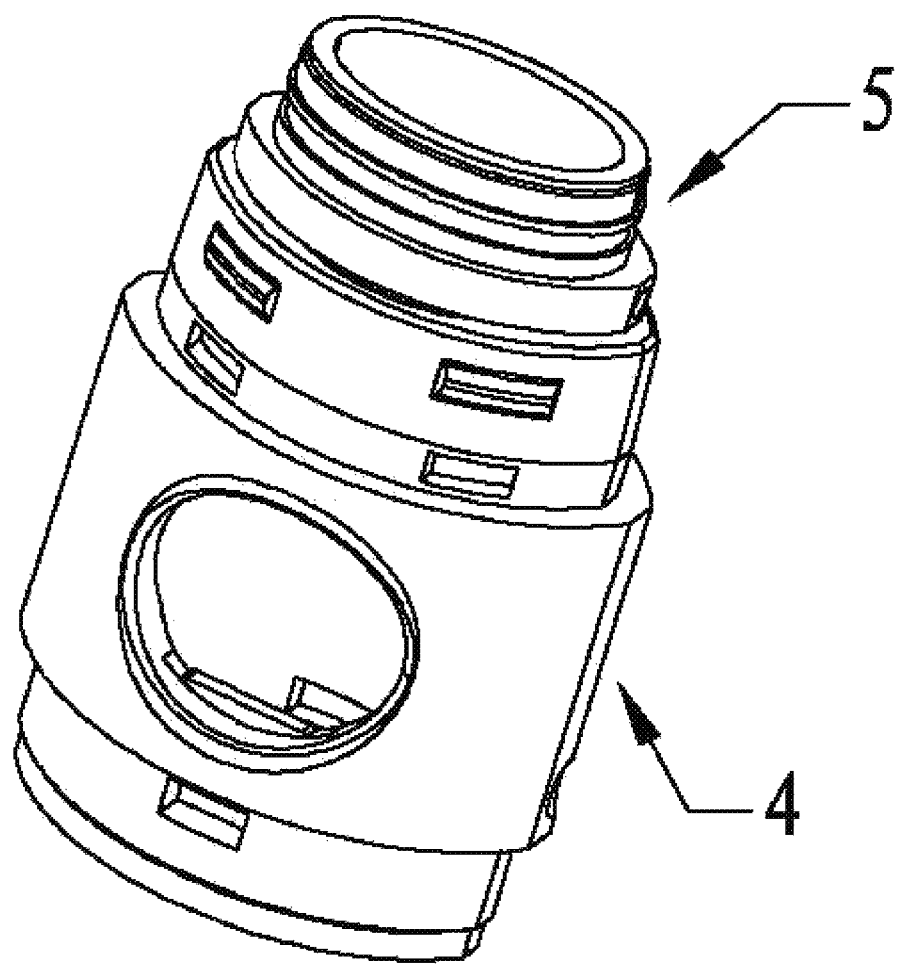

Referring to FIGS. 10 and 11, in another embodiment the vaporizer electrode assembly 6 is consisted of a column-shaped electrode fixer 63 inserted into a central through hole 54 of the circular protruding platform 53, a rod-like electrode 62 having a protruding ring at one end thereof and inserted into a central through hole 632 of the column-shaped electrode fixer 63, and a full-annular electrode 61 inserted into both an annular cavity 631 recessed along an outer circumference of the central through hole 632 of the electrode fixer 63 and an insertion groove 633 provided at a bottom of the annular cavity 631. The full-annular electrode 61 is consisted of a full-annular electrode plate 611 and two insertion electrode plate 612 protruding symmetrically and perpendicularly from the full-annular electrode plate 611.

Referring to FIGS. 1, 12, 13 and 14, a method of assembling the above-mentioned electronic cigarette, comprising aligning the protrusion 52 of the vaporizer connector 5 to the L-shaped grooves 423 of the battery connector 4; inserting the circular protruding platform 53 of the vaporizer assembly 2 into the circular cavity 422 of the battery connector 4; twisting the vaporizer connector 5 to a locking position so as to enable the positive and negative electrodes 41 of the battery connector 4 to be electrically connected to the semi-annular electrode 61 and the rod-like electrode 62 of the vaporizer connector 5, wherein the rod-like electrode 62 has a protruding ring at one end thereof; sheathing the vaporizer assembly 2 with the outer tube 3 of the vaporizer assembly 2; engaging the protrusion 4222 of the outer wall of the protruding platform 421 with the corresponding protrusion (not shown in the figures) of the outer tube of vaporizer assembly 3 to complete a snap fit therebetween.

All the above are the preferred embodiments of the present invention, and the invention is intended to cover various modifications and equivalent arrangements included within the scope of the invention.

What is claimed is:

1. An electronic cigarette comprising a battery assembly and a vaporizer assembly abutting the battery assembly, characterized in that
    a battery connector at a connecting end of the battery assembly and a vaporizer connector at a connecting end of the vaporizer assembly are connected via a twist lock joint, an electrode of the battery connector is electrically connected to an electrode of the vaporizer connector;
    the battery connector is consisted of a tube body and a protruding platform formed on one end of the tube body and having a cross-sectional area smaller than the tube body, wherein a circular cavity is provided at the center of the protruding platform, two recessed L-shaped grooves are radially and symmetrically formed in an inner wall of the circular cavity, a through hole is opened at a bottom of the circular cavity, positive and negative electrodes of the battery assembly are protruded out from the through hole, an outer wall of the protruding platform has a protrusion for snap fitting with a corresponding protrusion formed at an inner wall of one end of an outer tube of the vaporizer assembly;
    the vaporizer connector comprises a tube body and a circular protruding platform formed on one end of the tube body and having a cross-sectional area smaller than the tube body, two symmetrically-arranged protrusions protrude radially outward from an outer wall of the circular protruding platform, a center of the circular protruding platform is provided with a vaporizer electrode assembly comprising two electrodes;
    after the battery connector has been twist-lock connected with the vaporizer connector, the circular cavity of the battery connector exactly receives the circular protruding platform of the vaporizer connector, the L-shaped grooves of the battery connector tightly engage with the protrusions of the vaporizer connector, the positive and negative electrodes of the battery assembly are electrically connected to the two electrodes of the vaporizer electrode assembly;
    the vaporizer electrode assembly is consisted of a column-shaped electrode fixer inserted into a central through hole of the circular protruding platform, a rod-like electrode having a protruding ring at one end thereof and inserted into a central through hole of the column-shaped electrode fixer, and a semi-annular electrode or a full-annular electrode inserted into an annular cavity recessed along an outer circumference of the central through hole of the electrode fixer.

2. The electronic cigarette of claim 1, characterized in that the L-shaped groove is consisted of a vertical groove and an arc-shaped groove starting from a bottom half of the vertical groove and extending along a portion of the circumference of the inner wall of the circular cavity, wherein a height of the arc-shaped groove is slightly and gradually decreased.

3. The electronic cigarette of claim 2, characterized in that a lug is protruded downward from a top edge of the arc-shaped groove for locking purpose.

4. The electronic cigarette of claim 3, characterized in that the protrusion of the vaporizer connector has a concave portion configured to engage with the lug at the top edge of the arc-shaped groove.

5. The electronic cigarette of claim 1, characterized in that the positive and negative electrodes of the battery assembly are rod-like and retractable electrodes.

6. The electronic cigarette of claim 1, characterized in that the battery assembly, the vaporizer assembly and the outer tube of the vaporizer assembly all have non-circular cross sections.

7. The electronic cigarette of claim 6, characterized in that the non-circular cross section is oval cross section.

8. The electronic cigarette of claim 7, characterized in that an angle between the major axis X of an oval end surface of an oval protruding platform of the battery connector and a straight line between two midpoints of two vertical grooves of the symmetrically-arranged L-shaped grooves is an acute angle.

* * * * *